United States Patent [19]

Hahn

[11] Patent Number: 4,918,716
[45] Date of Patent: Apr. 17, 1990

[54] X-RAY EXAMINATION INSTALLATION HAVING TWO IMAGE PICK-UP UNITS

[75] Inventor: Alfred Hahn, Erlangen, Fed. Rep. of Germany

[73] Assignee: Siemens Aktiengesellschaft, Berlin and Munich, Fed. Rep. of Germany

[21] Appl. No.: 307,464

[22] Filed: Feb. 7, 1989

[30] Foreign Application Priority Data

Mar. 14, 1988 [DE] Fed. Rep. of Germany ....... 8803431

[51] Int. Cl.$^4$ ............................................. H05G 1/02
[52] U.S. Cl. .................................... 378/197; 378/193; 378/198
[58] Field of Search ......................... 378/193, 196–198

[56] References Cited

U.S. PATENT DOCUMENTS 4,501,011 2/1985 Hauck et al. ......................... 378/196
4,541,293 9/1985 Caugant et al. ..................... 378/197

FOREIGN PATENT DOCUMENTS 2117344 7/1972 France .
2120060 11/1983 United Kingdom .

OTHER PUBLICATIONS

"Biplane Multidirectional Angiocardiography": Exact Orthogonal Positioning of the X-Ray Systems (Laterally Mounted C-Arm-L-Arm-Systems), Wollschlager et al. Biomed. Technik 29 (1984, pp. 261–266).
Siemens Brochure "Das Uberlegene Systems Fur Biplane Angiokardiographie BICOR".

Primary Examiner—Janice A. Howell
Assistant Examiner—Don Wong
Attorney, Agent, or Firm—Hill, Van Santen, Steadman & Simpson

[57] ABSTRACT

An X-ray examination installation has two image pick-up units, and avoids the necessity of having a ceiling mount. The two image pick-up units are mounted on a common pedestal, pivotable around a common horizontal axis. The carrier for one of the image pick-up units is directly connected to the pedestal, and the carrier for the other of the pick-up units is connected to the pedestal via an intermediate carrier. Both image pick up units are adjustable in two planes by this installation.

6 Claims, 1 Drawing Sheet

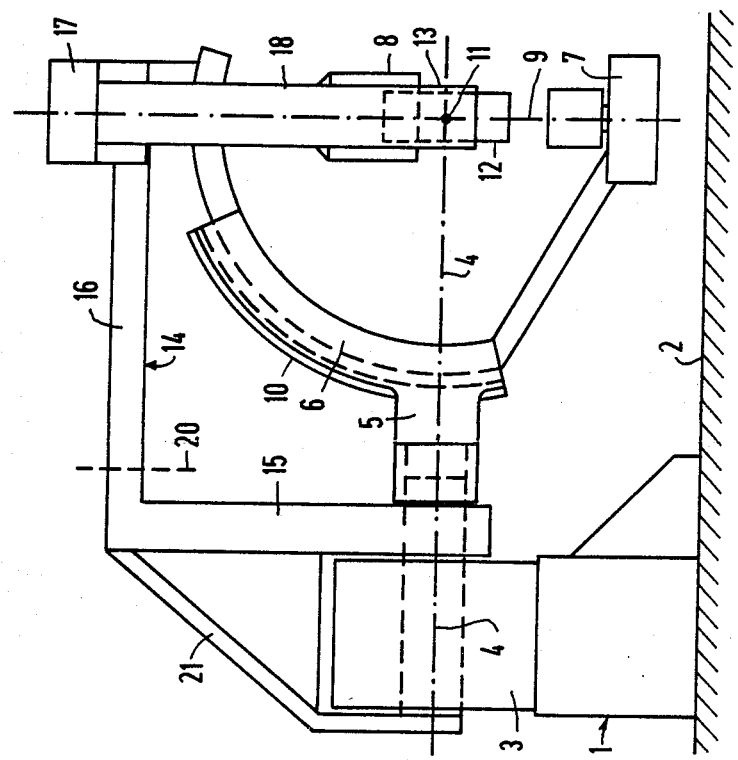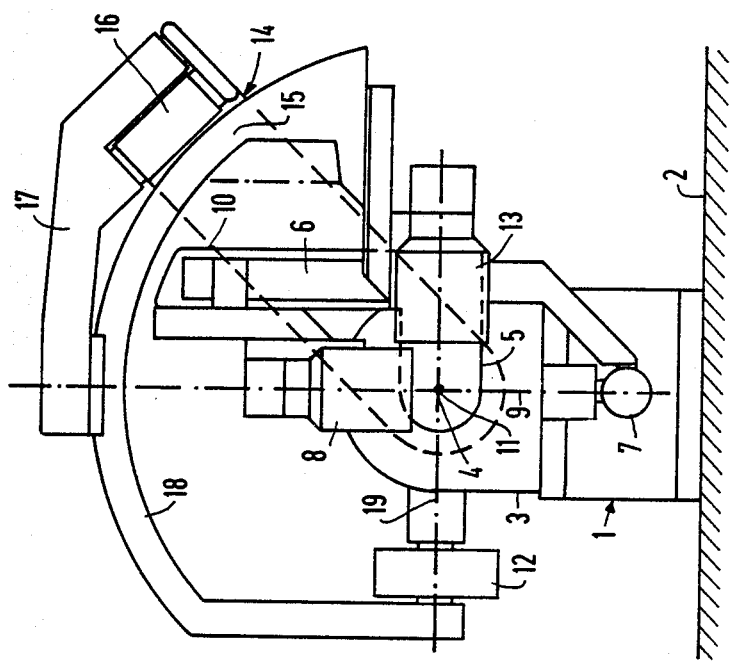

X-RAY EXAMINATION INSTALLATION HAVING TWO IMAGE PICK-UP UNITS

BACKGROUND OF THE INVENTION

1. Field of the Invention

The present invention is directed to an X-ray examination installation having two image pick-up units, each pick-up unit including a carrier with an X-ray source and an image receiver at opposite ends, with the X-ray source and the receiver being individually adjustable.

2. Description of the Prior Art

An X-ray examination installation having two image pick-up units, each consisting of a carrier with opposite ends at which an X-ray source and an image receiver are respectively mounted, with the source and receiver being individually adjustable, is known in the art. In this installation, one image pick-up unit is pivotably mounted at a pedestal, and the other image pick-up unit is pivotably mounted from a ceiling mount. The patient table is also suspended from the ceiling of the examination room. The combined ceiling and floor mounting results in a considerable structural outlay for this installation. Moreover, adjustment possibilities for auxiliary equipment such as, for example, a monitor, are limited by the ceiling mount for the second image pick-up unit.

SUMMARY OF THE INVENTION

It is an object of the present invention to provide an X-ray examination installation having two image pick-up units which avoids the use of a ceiling mount for one of the pick-up units.

It is a further object of the present invention to provide such an X-ray examination installation having a more compact structure and improved adjustment possibilities for auxiliary equipment than is currently possible with conventional installations.

The above and other objects are achieved in accordance with the principles of the present invention in an X-ray examination installation having two image pick-up units, wherein the two image pick-up units are mounted on a common pedestal pivotable around a common horizontal axis. The carrier for a first image pick-up unit is directly connected to the pedestal, and the carrier for a second image pick-up unit is connected to the pedestal via an intermediate carrier, so that the two image pick-up units are adjustable in two planes. The direct mounting of the carrier of the first image pick-up unit at the pedestal, and the use of an intermediate carrier for mounting the second image pick-up unit at the pedestal, make it possible to adjust both image pick-up units in two planes, perpendicular to each other, so that the central rays of the two image pick-up units are moved in the respective plane when the image pick-up units are adjusted. The intermediate carrier, and a holder for the carrier of the first image pick-up unit, are pivotably seated for rotation around the same axis. A compact structure having a single pedestal for both image pick-up units is achieved.

In one embodiment of the invention, a height-adjustable stand is provided as a part of the pedestal, so that the height of above the floor of both image pick-up units can be adjusted. This makes it possible to adjust the height of the common isocenter (i.e. point of intersection) of the central rays of the two image pick-up units and the swiveling axis.

Adjustment of the intermediate carrier for the second image pick-up unit in a circumferential direction in order to change the irradiation direction is not required in the installation disclosed herein because this irradiation direction can be varied by pivoting the second image pick-up unit around the common swiveling axis.

DESCRIPTION OF THE DRAWINGS

FIG. 1 is a side view of an X-ray examination installation constructed in accordance with the principles of the present invention.

FIG. 2 is an end view of the X-ray examination installation shown in FIG. 1.

DESCRIPTION OF THE PREFERRED EMBODIMENTS

As shown in the drawings, an X-ray examination installation constructed in accordance with the principles of the present invention includes a pedestal 1 supported on the floor 2 of an examination room. The pedestal 1 includes a height-adjustable stand 3. A horizontal axis 4 extends through the stand 3, and through a shoulder 5 of a holder 10 for a C-shaped carrier 6. The holder 10 is pivotable around the axis 4. An X-ray source 7 and an X-ray image intensifier 8 are mounted at the opposite ends of the carrier 6, and are aligned facing each other. The X-ray image intensifier 8 is mounted to the end of the carrier 6 so as to be adjustable in the direction of central ray 9. The central ray 9 is thus incident at the center of the input luminescent screen of the X-ray image intensifier 8. The carrier 6 is adjustable along its circumference within the holder 10, so that oblique transilluminations are possible. The central ray 9 intersects the axis 4 at an isocenter 11.

A second image pick-up unit is provided, consisting of an X-ray source 12, and an X-ray image intensifier 13. The second image pick-up unit is also pivotably seated for rotation around the horizontal axis 4, by means of an L-shaped intermediate carrier 14. The intermediate carrier 14 has a vertical leg 15 with an end pivotably mounted on the axis 4, and has a horizontal leg 16, which carries an arm 17. The free end of the arm 17 in turn carries a U-shaped carrier 18 having ends to which the x-ray source 12 and the x-ray image intensifier 13 are secured. The carrier 18, together with the end of the arm 17, are pivotably joined around an axis which intersects a central ray 19 of the x-ray source 12. This axis coincides with the central ray 9.

The arm 17 is fashioned as a carriage, and is thus displaceable along the leg 16 in the longitudinal direction. As a result, the second image pickup unit can be displaced to a standby position 20 close to the leg 15, and thus close to the pedestal 1.

The second image pickup unit is adjustable by pivoting the intermediate carrier 14 around the axis 4, so that the central ray 19 moves in a plane. The position or attitude of this plane in space is adjustable by pivoting the carrier 18 relative to the arm 17. The respective planes containing the central rays 9 and 19 intersect. The central rays 9 and 19 intersect at the isocenter 11 for every position of the first and second image pickup units. The isocenter 11 is adjustable in height by adjusting the height of the stand 3. The first and second image pickup units are thus also height-adjustable in common.

The intermediate carrier 14 is supported at the rear of the pedestal 1 by a support 21 through which the axis 4 extends, so that a stable mount results.

As can be seen in the drawings, the intermediate carrier 14 has its free leg extending over the first image pickup unit, parallel to the swiveling axis 4. The arm 17 proceeds at a right angle to the free leg 16. As a result, the first and second image pickup units do not impede each other when they are adjusted.

As shown in the drawings, the x-ray examination installation disclosed herein is a compact installation which permits examination of a patient in two intersecting planes with two image pickup units. A sealing suspension is not required for either of the image pickup units.

Although modifications and changes may be suggested by those skilled in the art it is the intention of the inventor to embody within the patent warranted hereon all changes and modifications as reasonably and properly come within the scope of his contribution to the art.

I claim as my invention:

1. An x-ray examination installation comprising:
   a first image pickup unit including a first carrier with opposite ends, and a first x-ray source and a first x-ray image receiver respectively mounted individually adjustable at said opposite ends of said first carrier;
   a second image pickup unit including a second carrier having opposite free ends and a second x-ray source and a second x-ray image receiver mounted individually adjustable at said opposite ends of said second carrier;
   a floor-mounted pedestal having a horizontal axis extending therethrough;
   means for directly mounting said first image pickup unit to said pedestal for rotation around said horizontal axis; and
   means for intermediately mounting said second image pickup unit to said pedestal for rotation around said horizontal axis so that said first and second image pickup units are individually adjustable in two respective planes.

2. An x-ray examination installation as claimed in claim 1 wherein said means for intermediately mounting comprises:
   an L-shaped intermediate carrier having a first leg with one end pivotably seated for rotation around said horizontal axis, said second carrier of said second image pickup unit being mounted to said second leg with said second leg extending over said first image pickup unit parallel to said horizontal axis.

3. An x-ray examination installation as claimed in claim 2 wherein said second carrier of said second image pickup unit is longitudinally displaceable along said second leg of said intermediate carrier.

4. An x-ray examination installation as claimed in claim 2 wherein said second carrier of said second image pickup unit is pivotably mounted to said second leg for rotation around an axis perpendicular to a central ray of said second image pickup unit.

5. An x-ray examination installation as claimed in claim 1 wherein said means for directly mounting said first image pickup unit is a holder pivotable around said horizontal axis.

6. An x-ray examination installation as claimed in claim 1 wherein said pedestal includes means for adjusting the height of both said first and second image pickup units in common.

* * * * *